US008883668B2

(12) United States Patent
Nesterenko et al.

(10) Patent No.: US 8,883,668 B2
(45) Date of Patent: Nov. 11, 2014

(54) PHOSPHORUS MODIFIED MOLECULAR SIEVES, THEIR USE IN CONVERSION OF ORGANICS TO OLEFINS

(75) Inventors: Nikolai Nesterenko, Nivelles (BE); Walter Vermeiren, Houthalen (BE); Delphine Minoux, Familleureux (BE); Sander Van Donk, Uccle (BE)

(73) Assignee: Total Research & Technology Feluy, Seneffe (Feluy) (BE)

( * ) Notice: Subject to any disclaimer, the term of this patent is extended or adjusted under 35 U.S.C. 154(b) by 840 days.

(21) Appl. No.: 12/671,217

(22) PCT Filed: Jul. 28, 2008

(86) PCT No.: PCT/EP2008/059883
§ 371 (c)(1),
(2), (4) Date: Jun. 22, 2010

(87) PCT Pub. No.: WO2009/016153
PCT Pub. Date: Feb. 5, 2009

(65) Prior Publication Data
US 2010/0292417 A1    Nov. 18, 2010

Related U.S. Application Data

(63) Continuation-in-part of application No. 12/097,537, filed as application No. PCT/EP2006/069697 on Dec. 14, 2006, now abandoned.

(30) Foreign Application Priority Data

Jul. 31, 2007    (EP) .................................... 07113545

(51) Int. Cl.
| | |
|---|---|
| *B01J 29/06* | (2006.01) |
| *C01B 33/24* | (2006.01) |
| *C07C 1/32* | (2006.01) |
| *C07C 1/26* | (2006.01) |
| *C01B 39/02* | (2006.01) |
| *C07C 1/20* | (2006.01) |
| *B01J 29/85* | (2006.01) |
| *C10G 3/00* | (2006.01) |
| *B01J 29/40* | (2006.01) |

(52) U.S. Cl.
CPC .............. *C01B 39/026* (2013.01); *C07C 1/322* (2013.01); *C07C 1/26* (2013.01); *C07C 1/20* (2013.01); *C10G 2300/202* (2013.01); *B01J 2229/36* (2013.01); *B01J 2229/37* (2013.01); *B01J 29/85* (2013.01); *C10G 3/00* (2013.01); *C10G 2300/4081* (2013.01); *C10G 2400/20* (2013.01); *B01J 29/40* (2013.01)
USPC .................. 502/60; 502/73; 502/78; 502/79; 502/85; 423/714

(58) Field of Classification Search
USPC ..................... 502/60, 73, 85, 78, 79; 423/714
See application file for complete search history.

(56) References Cited

U.S. PATENT DOCUMENTS

| | | | |
|---|---|---|---|
| 3,911,041 A | 10/1975 | Kaeding et al. | |
| 3,965,209 A * | 6/1976 | Butter et al. | ................... 585/454 |
| 4,356,338 A * | 10/1982 | Young | ............................ 585/407 |
| 4,456,780 A * | 6/1984 | Young | ............................ 585/475 |
| 4,522,929 A * | 6/1985 | Chester et al. | ................... 502/77 |
| 5,171,921 A | 12/1992 | Gaffney et al. | |
| 6,410,813 B1 | 6/2002 | Dath et al. | |

(Continued)

FOREIGN PATENT DOCUMENTS

| | | | |
|---|---|---|---|
| EP | 0 142 313 | * | 5/1985 |
| WO | 2007/068734 | * | 6/2007 |

OTHER PUBLICATIONS

Zhao et al: "Effect of Phosphous on HZSM-5 Catalyst for C4-olefin Cracking Reactions to Produce Propylene", Journal of Catalysis, Academic Press, Duluth, MN, US vol. 248, No. 1 (Apr. 23, 2007), pp. 29-37.

*Primary Examiner* — Elizabeth Wood

(57) ABSTRACT

The present invention is a phosphorous modified zeolite (A) made by a process comprising in that order:
 selecting a zeolite with low Si/Al ratio (advantageously lower than 30) among $H^+$ or $NH_4^+$-form of MFI, MEL, FER, MOR, clinoptilolite, said zeolite having been made preferably without direct addition of organic template;
 steaming at a temperature ranging from 400 to 870° C. for 0.01-200 h;
 leaching with an aqueous acid solution containing the source of P at conditions effective to remove a substantial part of Al from the zeolite and to introduce at least 0.3 wt % of P;
 separation of the solid from the liquid;
 an optional washing step or an optional drying step or an optional drying step followed by a washing step;
 a calcination step.

Figure 1:
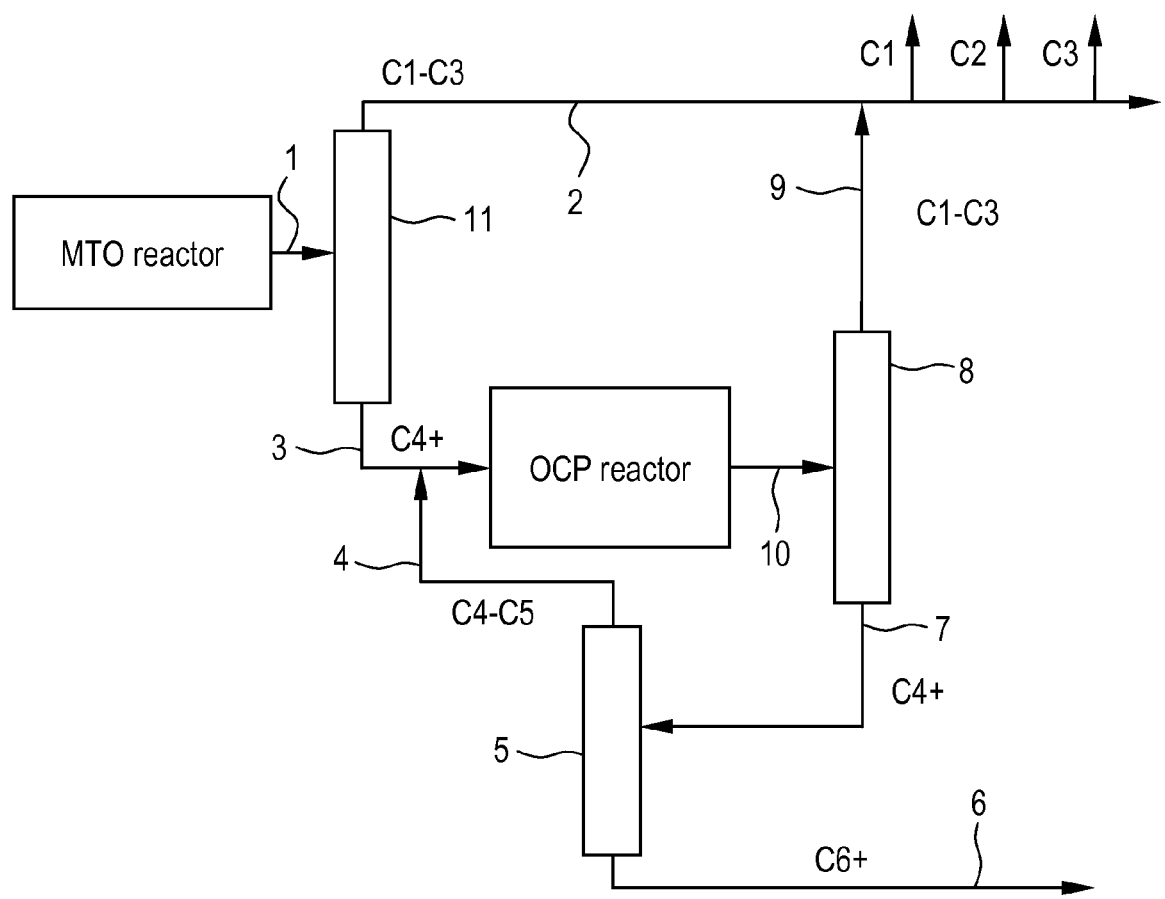

The present invention also relates to a process (hereunder referred as "XTO process") for making an olefin product from an oxygen-containing, halogenide-containing or sulphur-containing organic feedstock wherein said oxygen-containing, halogenide-containing or sulphur-containing organic feedstock is contacted with the above catalyst (in the XTO reactor) under conditions effective to convert at least a portion of the oxygen-containing, halogenide-containing or sulphur-containing organic feedstock to olefin products (the XTO reactor effluent).

The present invention also relates to a process (hereunder referred as "combined XTO and OCP process") to make light olefins from an oxygen-containing, halogenide-containing or sulphur-containing organic feedstock comprising : contacting said oxygen-containing, halogenide-containing or sulphur-containing organic feedstock in the XTO reactor with the above catalyst at conditions effective to convert at least a portion of the feedstock to form an XTO reactor effluent comprising light olefins and a heavy hydrocarbon fraction;
 separating said light olefins from said heavy hydrocarbon fraction;
 contacting said heavy hydrocarbon fraction in the OCP reactor at conditions effective to convert at least a portion of said heavy hydrocarbon fraction to light olefins.

21 Claims, 2 Drawing Sheets

(56) References Cited

U.S. PATENT DOCUMENTS

| | | | |
|---|---|---|---|
| 6,504,072 B1 * | 1/2003 | Brown et al. | 585/467 |
| 6,576,582 B1 * | 6/2003 | Beck et al. | 502/71 |
| 6,797,851 B2 * | 9/2004 | Martens et al. | 585/640 |
| 2003/0078463 A1 | 4/2003 | Martens et al. | |
| 2004/0254413 A1 | 12/2004 | Martens et al. | |
| 2005/0197245 A1 * | 9/2005 | Ghosh et al. | 502/71 |
| 2009/0216058 A1 * | 8/2009 | Dath et al. | 585/653 |

\* cited by examiner

PHOSPHORUS MODIFIED MOLECULAR SIEVES, THEIR USE IN CONVERSION OF ORGANICS TO OLEFINS

CROSS-REFERENCE TO RELATED APPLICATIONS

This application is National Stage entry of PCT/EP2008/059883, filed on Jul. 28, 2008, and this application is also a continuation in part of U.S. patent application Ser. No. 12/097,537 filed on Nov. 12, 2008, now abandoned which is a National Stage entry of PCT/EP2006/069697 filed on Dec. 14, 2006, which claims priority to EP Appl. Ser. No. 05112230.7 filed on Dec. 15, 2005.

FIELD OF THE INVENTION

The present invention relates to phosphorus modified molecular sieves as well as their use in conversion of organics to light olefins. More precisely the P-modified zeolites of the invention are obtained from crystalline aluminosilicates having been synthesized preferably without template. This provides a lower catalyst cost and makes a preparation procedure more environmentally friendly. The P-modified zeolites of the invention are useful as catalysts in a variety of processes including cracking, hydrocracking, isomerization, reforming, dewaxing, alkylation, transalkylation, conversion of oxygenates (or halogenide-containing or sulphur-containing organic compounds) to light olefins.

The limited supply and increasing cost of crude oil has prompted the search for alternative processes for producing hydrocarbon products. One such process is the conversion of oxygen-containing (by way of example methanol), halogenide-containing or sulphur-containing organic compounds to hydrocarbons and especially light olefins (by light olefins is meant $C_2$ to $C_4$ olefins) or gasoline and aromatics. In the present application the conversion of said oxygen-containing (also referred as oxygenates), halogenide-containing or sulphur-containing organic compounds to hydrocarbons and especially light olefins is referred as XTO process. The interest in the XTO process is based on the fact that feedstock's, especially methanol can be obtained from coal, biomass, hydrocarbon residues, petcoke, organic waste or natural gas by the production of synthesis gas which is then processed to produce methanol. The XTO process can be combined with an OCP (olefins cracking process) process to increase production of olefins. The XTO process produces light olefins such as ethylene and propylene as well as heavy hydrocarbons such as butenes and above. These heavy hydrocarbons are cracked in an OCP process to give mainly ethylene and propylene.

BACKGROUND OF THE INVENTION

In accordance with U.S. Pat. No. 3,911,041, methanol or dimethyl ether is subjected to the action, at a temperature of at least about 300° C., with a catalyst comprising a crystalline aluminosilicate zeolite having a silica to alumina ratio of at least about 12, a constraint index of about 1 to 12, and containing phosphorus incorporated with the crystal structure thereof in an amount of at least about 0.78 percent by weight. The amount of the phosphorus incorporated with the crystal structure of the zeolite may be as high as about 4.5 percent by weight. The zeolite, preferably, also has a dried crystal density of not less than about 1.6 grams per cubic centimeter. The crystalline aluminosilicate zeolite having a silica to alumina ratio of at least about 12 is first converted to the hydrogen form, then phosphorus is introduced by reaction with a phosphorus-containing compound having a covalent or ionic constituent capable of reacting or exchanging with hydrogen ion and thereafter heating. There is no steaming of the zeolite prior to introduction of phosphorus. Preferably, prior to reacting the zeolite with the phosphorus-containing compound, the zeolite is dried. Drying can be effected in the presence of air. Elevated temperatures may be employed.

In accordance with U.S. Pat. No. 5,573,990 methanol and/or dimethylether is converted in presence of a catalyst which contains at least 0.7% by weight of phosphorus and at least 0.97% by weight of rare earth elements incorporated within the structure of the catalyst. Preferably the amount of phosphorus is comprised between 0.7 and 5% by weight. The phosphorus content in the catalyst is most preferably comprised between 1.3 and 1.7% by weight. The rare earth elements incorporated with the crystal structure of the catalyst are preferably rich in lanthanum, the content of lanthanum in the catalyst being preferably comprised between 2.5 and 3.5% by weight. The zeolite ZSM-5 based catalyst presents a mole ratio $SiO_2/Al_2O_3$ comprised between 40 and 80, a crystal size comprised between 1 and 10 µm and adsorption capacities of n-hexane and water 10-11% by weight and 6-7% by weight respectively. Said ZSM-5 is synthesized in the presence of a template, then is converted to the hydrogen form by ion exchange with hydrochloric acid. The zeolite HZSM-5 prepared as described above is impregnated in aqueous phosphoric acid solution under reduced pressure preferably comprised between 0.08 and 0.09MPa for 2-3 hours. It is dried at <110° C. for 3-5 hours and calcined at about 540° C. for about 3 hours, the phosphorus content of the obtained product PZSM-5 being 0.7-5% (by weight). There is no steaming of the zeolite prior to introduction of phosphorus. The feedstock methanol comprises steam in a ratio methanol/steam 10-50/90-50, the examples are made with a ratio 30/70.

U.S. Pat. No. 6,797,851 uses at least two different zeolite catalysts to produce an olefin composition from an oxygenate, for example, two different ZSM-type catalysts, to produce olefin having a significant quantity of ethylene and propylene. The catalysts can be mixed together in one reactor, arranged in separate beds, or used in separate reactors in series. It is desirable that one of the zeolite catalysts contains a ZSM-5 molecular sieve. The ZSM-5 molecular sieve is selected from the group consisting of an unmodified ZSM-5, a phosphorous modified ZSM-5, a steam modified ZSM-5 having a micropore volume reduced to not less than 50% of that of the unsteamed ZSM-5, and mixtures thereof. It is also desirable to have a second zeolite catalyst which contains a zeolite molecular sieve selected from the group consisting of 10-ring zeolites such as ZSM-22, ZSM-23, ZSM-35, ZSM-48, and a mixture thereof. In one embodiment, the zeolite employed in the first stage of the above process is ZSM-5 having a silica to alumina molar ratio of at least 250, as measured prior to any treatment of the zeolite to adjust its diffusivity. According to one embodiment, the zeolite is modified with a phosphorous containing compound to control reduction in pore volume. Alternatively, the zeolite is steamed, and the phosphorous compound is added prior to or after steaming. After contacting with the phosphorus-containing compound, the porous crystalline material, according to one embodiment, is dried and calcined to convert the phosphorus to an oxide form. One or more inert diluents may be present in the oxygenate feedstock. Preferred diluents are water and nitrogen. Water can be injected in either liquid or vapor form. For example, the process may be conducted in the presence of water such that the molar ratio water to methanol in the feed is from about 0.01:1 to about 10:1.

US20060106270A1, now issued as U.S. Pat. No. 7,408, 092, relates to a process wherein the average propylene cycle selectivity of an oxygenate to propylene (OTP) process using a dual-function oxygenate conversion catalyst is substantially enhanced by the use of a combination of: 1) moving bed reactor technology in the hydrocarbon synthesis portion of the OTP flow scheme in lieu of the fixed bed technology of the prior art; 2) a hydrothermally stabilized and dual-functional catalyst system comprising a molecular sieve having dual-function capability dispersed in a phosphorus-modified alumina matrix containing labile phosphorus and/or aluminum anions; and 3) a catalyst on-stream cycle time of 400 hours or less. The use of a mixture of a zeolitic catalyst system with a non-zeolitic catalyst system is described. This mixed catalyst embodiment can be accomplished either using a physical mixture of particles containing the zeolitic material with particles containing the non-zeolitic material or the catalyst can be formulated by mixing the two types of material into the phosphorus modified aluminum matrix in order to form particles having both ingredients present therein. In either case the preferred combination is a mixture of ZSM-5 or ZSM-11 with SAPO-34 in relative amounts such that ZSM-5 or ZSM-11 comprises 30 to 95 wt % of the molecular sieve portion of the mixture with a value of about 50 to 90 wt % being especially preferred. It doesn't describe phosphorus modified molecular sieves. A diluent is preferably used in order to control partial pressure of the oxygenate reactant in the OTP conversion zone and in order to shift the overall reaction selectivity towards propylene. An especially preferred diluent for use is steam since it is relatively easily recovered from the product effluent stream utilizing condensation techniques. The amount of diluent used will be selected from the range from about 0.1:1 to 5:1 moles of diluent per mole of oxygenate and preferably 0.5:1 to 2:1 in order to lower the partial pressure of the oxygenates to a level which favours production of propylene.

EP448000 relates to a process for the conversion of methanol or dimethylether into light olefins in presence of water vapour over a silicoaluminate of the pentasil structure of at least Si/Al ratio of 10, producing at least 5 wt % of ethylene, at least 35 wt % of propylene and at most 30 wt % butenes by (1) using a total pressure of 10 to 90 kPa, (2) a weight ratio of water to methanol of 0.1 to 1.5, (3) a reactor temperature of 280 to 570° C. and (4) a proton-containing catalyst of the pentasil-type, having an alkali-content of at most 380 ppm, less than 0.1 wt % of ZnO and less than 0.1 wt % of CdO and a BET surface area of 300 to 600 m2/gram and a pore volume of 0.3 to 0.8 cm3/gram.

The phosphorus modified molecular sieves of the present invention is prepared based on zeolite with low Si/Al ratio (advantageously below 30) preferably synthesized without direct addition of organic template, then the zeolite is subjected to a steam treatment at high temperature before a leaching step with acid solution containing the source of phosphorus which removes advantageously at least 10% of the Al from the zeolite and which leads to at least 0.3 wt % of P on the zeolite. It has been found that phosphorus acid are very efficient in complexing the extra-framework aluminiumoxides and hence removing them from the zeolite solid material. Unexpectedly, a larger quantity of phosphorus than what could be expected from the typical pore volume of the zeolite and assuming that the pores of the zeolites are filled with the used phosphoric acid solution, stays in the solid zeolite material. The chemical functionalities of aluminum with phosphorus in the P-zeolite inhibit the further dealumination of zeolites, which, in turn, increases their stability and selectivity.

The zeolite can be MFI, MOR, MEL, clinoptilolite or FER crystalline aluminosilicate molecular sieves having a low initial Si/Al ratio (advantageously below 30) and preferably synthesized without direct addition of organic directing agent.

The method consists in steaming followed by leaching by a solution of phosphoric acid or by any acid solution containing the source of P. It is generally known by the persons in the art that steam treatment of zeolites, results in aluminium that leaves the zeolite framework and resides as aluminiumoxides in and outside the pores of the zeolite. This transformation is known as dealumination of zeolites and this term will be used throughout the text. The treatment of the steamed zeolite with an acid solution results in dissolution of the extra-framework aluminiumoxides. This transformation is known as leaching and this term will be used throughout the text. Then the zeolite is separated, advantageously by filtration, and optionally washed. A drying step can be envisaged between filtering and washing steps. The solution after the washing can be either separated, by way of example, by filtering from the solid or evaporated.

The residual P-content is adjusted by P-concentration in the leaching solution, drying conditions, and washing procedure if any. This procedure leads to dealumination of zeolites and retention of P. Advantageously, at least 0.3 wt % of P is retained after dealumination on zeolite. Both factors dealumination and the retention of P stabilize the lattice aluminium in the zeolitic lattice, thus avoiding further dealumination. This leads to higher hydrothermal stability, tuning of molecular sieves properties and adjustment of acid properties. The degree of dealumination can be adjusted by the steaming and leaching conditions.

The P-modified zeolites of this recipe are obtained based on cheap crystalline alumosilicates with low Si/Al ratio preferably synthesized without direct addition of organic template. This provides a lower final catalyst cost and makes a preparation procedure more environmentally friendly. The recipe simplifies the procedure for P-ZSM preparation and allows adjusting the Si/Al ratio and P-content in the catalyst. The catalysts show high C3-yield, high C3-/C2-ratio, high stability, high C3's purity and reduced selectivity to paraffin's and to aromatic in XTO. These catalysts provide also the additional flexibility for ethylene and C4+ recycling for additional propylene production. The average propylene yield can be substantially enhanced by using these catalysts in a combination of XTO and OCP process.

BRIEF DESCRIPTION OF THE INVENTION

The present invention is a phosphorous modified zeolite (A) made by a process comprising in that order:
   selecting a zeolite with low Si/Al ratio (advantageously lower than 30) among $H^+$ or $NH_4^+$-form of MFI, MEL, FER, MOR, clinoptilolite, said zeolite having been made preferably without direct addition of organic template;
   steaming at a temperature ranging from 400 to 870° C. for 0.01-200 h;
   leaching with an aqueous acid solution containing the source of P at conditions effective to remove a substantial part of Al from the zeolite and to introduce at least 0.3 wt % of P;
   separation of the solid from the liquid;
   an optional washing step or an optional drying step or an optional drying step followed by a washing step;
   a calcination step.

The zeolite can be made with the help of seeds techniques but without template, the seeds could have been made with a template which means that the zeolite is made without direct addition of a template.

Advantageously the steaming step and the leaching step are consecutive, there is no intermediate steps such as, by way of example, contact with silica powder and drying.

Further to the leaching, the separation of the liquid from the solid is advantageously made by filtering at a temperature between 0-90° C., centrifugation at a temperature between 0-90° C., evaporation or equivalent.

Optionally, the zeolite can be dried after separation before washing. Advantageously said drying is made at a temperature between 40-600° C. for 1-10 h. This drying can be processed either in a static condition or in a gas flow. Air, nitrogen or any inert gases can be used. Optionally further to the leaching step and the separation the zeolite is dried at a temperature between 40 and 600° C.

The washing step can be performed either during the filtering (separation step) with a portion of cold (<40° C.) or hot water (>40 but <90° C.) or the solid can be subjected to a water solution (1 kg of solid/4 liters water solution) and treated under reflux conditions for 0.5-10 h followed by evaporation or filtering.

Final calcination step is performed advantageously at the temperature 400-700° C. either in a static condition or in a gas flow. Air, nitrogen or any inert gases can be used.

Advantageously (A) when contacted with an oxygen-containing, halogenide-containing or sulphur-containing organic feedstock is capable to make an olefin product.

The present invention also relates to catalyst consisting of the above (A) or comprising the above (A).

The present invention also relates to a process (hereunder referred as "XTO process") for making an olefin product from an oxygen-containing, halogenide-containing or sulphur-containing organic feedstock wherein said oxygen-containing, halogenide-containing or sulphur-containing organic feedstock is contacted with the above catalyst (in the XTO reactor) under conditions effective to convert at least a portion of the oxygen-containing, halogenide-containing or sulphur-containing organic feedstock to olefin products (the XTO reactor effluent). It is desirable to have a substantially 100% conversion of the organic compound in the XTO reactor. This conversion rate is adjusted by optimization of contact time and the frequency of regeneration of the catalyst.

According to a specific embodiment the XTO reactor effluent comprising light olefins and a heavy hydrocarbon fraction is sent to a fractionation section to separate said light olefins from said heavy hydrocarbon fraction; said heavy hydrocarbon fraction is recycled in the XTO reactor at conditions effective to convert at least a portion of said heavy hydrocarbon fraction to olefin products.

With regards to said effluent of the XTO process, "light olefins" means ethylene and propylene and the "heavy hydrocarbon fraction" is defined herein as the fraction containing hydrocarbons having a molecular weight greater than propane, which means hydrocarbons having 4 carbon atoms or more and written as $C_4^+$.

According to another embodiment of the invention said olefin products (the effluent of the XTO) are fractionated to form a stream comprising essentially ethylene and at least a part of said stream is recycled in the XTO reactor to increase the propylene production and then the flexibility of ethylene vs propylene production.

According to another embodiment of the invention both ethylene and the C4+ can be recycled in the XTO reactor.

The present invention also relates to a process (hereunder referred as "combined XTO and OCP process") to make light olefins from an oxygen-containing, halogenide-containing or sulphur-containing organic feedstock comprising:

contacting said oxygen-containing, halogenide-containing or sulphur-containing organic feedstock in the XTO reactor with the above catalyst at conditions effective to convert at least a portion of the feedstock to form an XTO reactor effluent comprising light olefins and a heavy hydrocarbon fraction;

separating said light olefins from said heavy hydrocarbon fraction;

contacting said heavy hydrocarbon fraction in the OCP reactor at conditions effective to convert at least a portion of said heavy hydrocarbon fraction to light olefins. It is desirable to have a substantially 100% conversion of the organic compound in the XTO reactor. This conversion rate is adjusted by optimization of contact time and the frequency of regeneration of the catalyst.

DETAILED DESCRIPTION OF THE INVENTION

As regards (A) and the selected zeolite, advantageously it is a crystalline alumosilicate of the MFI family or the MEL family. An example of MFI silicates is ZSM-5. An example of an MEL zeolite is ZSM-11 which is known in the art. Other examples are described by the International Zeolite Association (*Atlas of Zeolite Structure Types*, 1987, Butterworths).

Crystalline silicates are microporous crystalline inorganic polymers based on a framework of $XO_4$ tetrahydra linked to each other by sharing of oxygen ions, where X may be trivalent (e.g. Al, B, ... ) or tetravalent (e.g. Ge, Si, ... ). The crystal structure of a crystalline silicate is defined by the specific order in which a network of tetrahedral units are linked together. The size of the crystalline silicate pore openings is determined by the number of tetrahedral units, or, alternatively, oxygen atoms, required to form the pores and the nature of the cations that are present in the pores. They possess a unique combination of the following properties: high internal surface area; uniform pores with one or more discrete sizes; ion exchangeability; good thermal stability; and ability to adsorb organic compounds. Since the pores of these crystalline alumosilicates are similar in size to many organic molecules of practical interest, they control the ingress and egress of reactants and products, resulting in particular selectivity in catalytic reactions. Crystalline alumosilicates with the MFI structure possess a bi-directional intersecting pore system with the following pore diameters: a straight channel along [010]:0.53-0.56 nm and a sinusoidal channel along [100]:0.51-0.55 nm. Crystalline alumosilicates with the MEL structure possess a bi-directional intersecting straight pore system with straight channels along [100] having pore diameters of 0.53-0.54 nm.

Advantageously the selected MFI, MEL, FER, MOR, clinoptilolite (or $H^+$ or NH4+-form MFI, MEL, FER, MOR, clinoptilolite) has an initial atomic ratio Si/Al of 30 or lower and preferably ranging from 4 to 30. The conversion to the $H^+$ or $NH_4$+-form is known per se and is described in U.S. Pat. Nos. 3,911,041 and 5,573,990.

In the steam treatment step, the temperature is preferably from 420 to 870° C., more preferably from 480 to 760° C. The pressure is preferably atmospheric pressure and the water partial pressure may range from 13 to 100 kPa. The steam atmosphere preferably contains from 5 to 100 vol % steam with from 0 to 95 vol % of an inert gas, preferably nitrogen. The steam treatment is preferably carried out for a period of from 0.05 to 200 hours, more preferably from 0.05 to 50 hours. The steam treatment tends to reduce the amount of tetrahedral aluminium in the crystalline silicate framework by forming alumina.

The leaching with an aqueous acid solution containing the source of P is advantageously made under reflux conditions, meaning boiling temperature of the solution.

Amount of said acid solution is advantageously between 2 and 10 liters per kg of zeolite. A typical leaching period is around 0.5 to 24 hours. Advantageously the aqueous acid solution containing the source of P in the leaching step has a pH of 3, advantageously 2, or lower. Advantageously said aqueous acid solution is phosphorus acids, a mixture of phosphorus acids and organic or inorganic acid or mixtures of salts of phosphorus acids and organic or inorganic acids. The phosphorus acids or the corresponding salts can be of the phosphate ($[PO_4]^{3-}$, being tribasic), phosphite ($[HPO_3]^{2-}$, being dibasic), or hypophosphite ($[H_2PO_2]^{1-}$, being monobasic), type. Of the phosphate type also di or polyphosphates ($[P_nO_{3n+1}]^{(n+2)-}$) can be used. The other organic acids may comprise an organic acid such as citric acid, formic acid, oxalic acid, tartaric acid, malonic acid, succinic acid, glutaric acid, adipic acid, maleic acid, phthalic acid, isophthalic acid, fumaric acid, nitrilotriacetic acid, hydroxyethylenediaminetriacetic acid, ethylenediaminetetracetic acid, trichloroacetic acid trifluoroacetic acid or a salt of such an acid (e.g. the sodium salt) or a mixture of two or more of such acids or salts. The other inorganic acids may comprise an inorganic acid such as nitric acid, hydrochloric acid, methansulfuric acid, sulfuric acid or a salt of such an acid (e.g. the sodium or ammonium salts) or a mixture of two or more of such acids or salts.

Advantageously the final P-content of (A) is at least 0.3 wt % and preferably between 0.3 and 7 w %. Advantageously at least 10% of Al, in respect to parent zeolite MFI, MEL, FER, MOR and clinoptilolite, have been extracted and removed from the zeolite by the leaching. The residual P-content is adjusted by P-concentration in the leaching solution, drying conditions and a washing procedure if any. A drying step can be envisaged between filtering and washing steps.

Then the zeolite either is separated from the washing solution or is dried without separation from the washing solution. Said separation is advantageously made by filtration. Then the zeolite is calcined, by way of example, at 400° C. for 2-10 hours.

The solid (A) of the present invention can be used as itself as a catalyst. In another embodiment it can be formulated into a catalyst by combining with other materials that provide additional hardness or catalytic activity to the finished catalyst product. Materials which can be blended with (A) can be various inert or catalytically active materials, or various binder materials. These materials include compositions such as kaolin and other clays, various forms of rare earth metals, phosphates, alumina or alumina sol, titania, zirconia, quartz, silica or silica sol, and mixtures thereof. These components are effective in densifying the catalyst and increasing the strength of the formulated catalyst. The catalyst may be formulated into pellets, spheres, extruded into other shapes, or formed into a spray-dried particles. The amount of (A) which is contained in the final catalyst product ranges from 10 to 90 weight percent of the total catalyst, preferably 20 to 70 weight percent of the total catalyst.

With regards to the XTO process, the catalyst of the invention is particularly suited for the catalytic conversion of oxygen-containing, halogenide-containing or sulphur-containing organic compounds to hydrocarbons. Accordingly, the present invention also relates to a method for making an olefin product from an oxygen-containing, halogenide-containing or sulphur-containing organic feedstock wherein said oxygen-containing, halogenide-containing or sulphur-containing organic feedstock is contacted with the above catalyst under conditions effective to convert the oxygen-containing, halogenide-containing or sulphur-containing organic feedstock to olefin products (the effluent of the XTO). Said effluent comprises light olefins and a heavy hydrocarbon fraction.

In this process a feedstock containing an oxygen-containing, halogenide-containing or sulphur-containing organic compound contacts the above described catalyst in a reaction zone of a reactor at conditions effective to produce light olefins, particularly ethylene and propylene. Typically, the oxygen-containing, halogenide-containing or sulphur-containing organic feedstock is contacted with the catalyst when the oxygen-containing, halogenide-containing or sulphur-containing organic compounds is in vapour phase. Alternately, the process may be carried out in a liquid or a mixed vapour/liquid phase. In this process, converting oxygen-containing, halogenide-containing or sulphur-containing organic compounds, olefins can generally be produced at a wide range of temperatures. An effective operating temperature range can be from about 200° C. to 700° C. At the lower end of the temperature range, the formation of the desired olefin products may become markedly slow. At the upper end of the temperature range, the process may not form an optimum amount of product. An operating temperature of at least 300° C., and up to 600° C. is preferred.

The pressure also may vary over a wide range. Preferred pressures are in the range of about 5 kPa to about 5 MPa, with the most preferred range being of from about 50 kPa to about 0.5 MPa. The foregoing pressures refer to the partial pressure of the oxygen-containing, halogenide-containing, sulphur-containing organic compounds and/or mixtures thereof.

The process can be carried out in any system using a variety of transport beds, although a fixed bed or moving bed system could be used. Advantageously a fluidized bed is used. It is particularly desirable to operate the reaction process at high space velocities. The process can be conducted in a single reaction zone or a number of reaction zones arranged in series or in parallel. Any standard commercial scale reactor system can be used, for example fixed bed, fluidised or moving bed systems. After a certain time on—stream the catalyst needs to be regenerated. This regeneration can be carried out in a separate reactor or in the same reactor. In case of a moving bed or fluidised bed reactor, a part of the catalyst is continuously or intermittently withdrawn from the conversion reactor and sent to a second reactor for regeneration. After the regeneration, the regenerated catalyst is continuously or intermittently sent back to the conversion reactor. In case of fixed bed reactor the reactor is taken off-line for regeneration. Generally this requires a second spare reactor that can take over the conversion into light olefins. After regeneration the fixed bed reactor is in stand-by until the spare reactor needs regeneration and the regenerated reactor takes over the conversion. Regeneration is carried out by injecting an oxygen-containing stream over the catalyst at sufficient high temperature to burn the deposited coke on the catalyst. The commercial scale reactor systems can be operated at a weight hourly space velocity (WHSV) of from 0.1 $hr^{-1}$ to 1000 $hr^{-1}$.

One or more inert diluents may be present in the feedstock, for example, in an amount of from 1 to 95 molar percent, based on the total number of moles of all feed and diluent components fed to the reaction zone. Typical diluents include, but are not necessarily limited to helium, argon, nitrogen, carbon monoxide, carbon dioxide, hydrogen, water, paraffins, alkanes (especially methane, ethane, and propane), aromatic compounds, and mixtures thereof. The preferred diluents are water and nitrogen. Water can be injected in either liquid or vapour form.

According to a specific embodiment essentially no water (or steam) is injected as diluent of the feedstock sent to the XTO reactor. However it means that the feedstock can contain the water already contained in the fresh oxygen-containing, halogenide-containing or sulphur-containing organic feedstock or the steam used to engage proper flowing of catalyst in fluidised bed of moving bed reactors of the XTO reactor.

The oxygenate feedstock is any feedstock containing a molecule or any chemical having at least an oxygen atom and capable, in the presence of the above catalyst, to be converted to olefin products. The oxygenate feedstock comprises at least one organic compound which contains at least one oxygen atom, such as aliphatic alcohols, ethers, carbonyl compounds (aldehydes, ketones, carboxylic acids, carbonates, esters and the like). Representative oxygenates include but are not necessarily limited to lower straight and branched chain aliphatic alcohols and their unsaturated counterparts. Examples of suitable oxygenate compounds include, but are not limited to: methanol; ethanol; n-propanol; isopropanol; $C_4$-$C_{20}$ alcohols; methyl ethyl ether; dimethyl ether; diethyl ether; di-isopropyl ether; formaldehyde; dimethyl carbonate; dimethyl ketone; acetic acid; and mixtures thereof. Representative oxygenates include lower straight chain or branched aliphatic alcohols, their unsaturated counterparts. Analogously to these oxygenates, compounds containing sulphur or halides may be used. Examples of suitable compounds include methyl mercaptan; dimethyl sulfide; ethyl mercaptan; di-ethyl sulfide; ethyl monochloride; methyl monochloride, methyl dichloride, n-alkyl halides, n-alkyl sulfides having n-alkyl groups of comprising the range of from about 1 to about 10 carbon atoms; and mixtures thereof. Preferred oxygenate compounds are methanol, dimethyl ether, or a mixture thereof.

In XTO effluent among the olefins having 4 carbon atoms or more there are greater than 50 weight % of butenes. More than 80% by weight and advantageously more than 85% of the hydrocarbons having 4 carbon atoms or more are C4 to C8 olefins.

According to a specific embodiment the XTO reactor effluent comprising light olefins and a heavy hydrocarbon fraction is sent to a fractionation section to separate said light olefins from said heavy hydrocarbon fraction; said heavy hydrocarbon fraction is recycled in the XTO reactor at conditions effective to convert at least a portion of said heavy hydrocarbon fraction to olefin products.

With regards to said effluent of the XTO process, "light olefins" means ethylene and propylene and the "heavy hydrocarbon fraction" is defined herein as the fraction containing hydrocarbons having a molecular weight greater than propane, which means hydrocarbons having 4 carbon atoms or more and written as $C_4^+$.

According to another embodiment of the invention said olefin products (the effluent of the XTO) are fractionnated to form a stream comprising essentially ethylene and at least a part of said stream is recycled in the XTO reactor to increase the propylene production and then the flexibility of ethylene vs propylene production. Advantageously the ratio of ethylene to the oxygen-containing, halogenide-containing or sulphur-containing organic feedstock is 1.8 or less.

According to another embodiment of the invention both ethylene and the C4+ can be recycled in the XTO reactor.

The present invention also relates to a process (hereunder referred as "combined XTO and OCP process") to make light olefins from an oxygen-containing, halogenide-containing or sulphur-containing organic feedstock comprising:

contacting said oxygen-containing, halogenide-containing or sulphur-containing organic feedstock in the XTO reactor with the above catalyst at conditions effective to convert at least a portion of the feedstock to form an XTO reactor effluent comprising light olefins and a heavy hydrocarbon fraction;

separating said light olefins from said heavy hydrocarbon fraction;

contacting said heavy hydrocarbon fraction in the OCP reactor at conditions effective to convert at least a portion of said heavy hydrocarbon fraction to light olefins.

The effluent of the XTO reactor comprising light olefins and a heavy hydrocarbon fraction is sent to a fractionation section to separate said light olefins from said heavy hydrocarbon fraction. With regards to said effluent of the XTO process, "light olefins" means ethylene and propylene and the "heavy hydrocarbon fraction" is defined herein as the fraction containing hydrocarbons having a molecular weight greater than propane, which means hydrocarbons having 4 carbon atoms or more and written as $C_4^+$. It is desirable to have a substantially 100% conversion of the organic compound in the primary reactor. This conversion rate is adjusted by optimization the contact time and the frequency of the regeneration of the catalyst.

With regards to the OCP process, said process is known per se. It has been described in EP 1036133, EP 1035915, EP 1036134, EP 1036135, EP 1036136, EP 1036138, EP 1036137, EP 1036139, EP 1194502, EP 1190015, EP 1194500 and EP 1363983 the content of which are incorporated in the present invention. The heavy hydrocarbon fraction produced in the XTO reactor is converted in the OCP reactor, also called an "olefin cracking reactor" herein, to produce additional amounts of ethylene and propylene.

According to a specific embodiment the catalysts found to produce this conversion comprise a crystalline alumosilicate of the MFI family or the MEL family. These alumosilicates have been described above in the description of (A).

According to a specific embodiment of the invention the catalysts found to produce this heavy conversion are the catalysts consisting of the above (A) or comprising the above (A). They can be the same as the catalysts of the XTO reactor or although they are in the description of (A) they can be different of the XTO catalyst because of the starting zeolite, the P content etc . . .

According to another embodiment the catalysts found to produce this heavy conversion are disclosed in the patents EP 1036133, EP 1035915, EP 1036134, EP 1036135, EP 1036136, EP 1036138, EP 1036137, EP 1036139, EP 1194502, EP 1190015, EP 1194500 and EP 1363983.

The crystalline alumosilicate catalyst has structural and chemical properties and is employed under particular reaction conditions whereby the catalytic cracking of the $C_4^+$ olefins readily proceeds. Different reaction pathways can occur on the catalyst. Under the process conditions, having an inlet temperature of around 400° to 600° C., preferably from 520° to 600° C., yet more preferably 540° to 580° C., and an olefin partial pressure of from 0.1 to 2 bars, most preferably around atmospheric pressure. Olefin catalytic cracking may be understood to comprise a process yielding shorter molecules via bond breakage.

The MFI catalyst having a high silicon/aluminum atomic ratio for use in the OCP reactor of the present invention may be manufactured by removing aluminum from a commercially available crystalline silicate. A typical commercially available silicalite has a silicon/aluminum atomic ratio of around 120. The commercially available MFI crystalline silicate may be modified by a steaming process which reduces the tetrahedral aluminum in the crystalline silicate framework and converts the aluminum atoms into octahedral aluminum in the form of amorphous alumina. Although in the steaming step aluminum atoms are chemically removed from the crystalline silicate framework structure to form alumina particles, those particles cause partial obstruction of the pores or channels in the framework. This inhibits the olefinic cracking processes of the present invention. Accordingly, following the steaming step, the crystalline silicate is subjected to an extraction step wherein amorphous alumina is removed from the pores and the micropore volume is, at least partially, recovered. The physical removal, by a leaching step, of the amorphous alumina from the pores by the formation of a water-soluble aluminum complex yields the overall effect of de-alumination of the MFI crystalline silicate. In this way by removing aluminum from the MFI crystalline silicate framework and then removing alumina formed there from the pores, the process aims at achieving a substantially homogeneous de-alumination throughout the whole pore surfaces of the catalyst. This reduces the acidity of the catalyst and thereby reduces the occurrence of hydrogen transfer reactions in the cracking process. The reduction of acidity ideally occurs substantially homogeneously throughout the pores defined in the crystalline silicate framework. This is because in the olefin-cracking process hydrocarbon species can enter deeply into the pores. Accordingly, the reduction of acidity and thus the reduction in hydrogen transfer reactions which would reduce the stability of the MFI catalyst are pursued throughout the whole pore structure in the framework. The framework silicon/aluminum ratio may be increased by this process to a value of at least about 180, preferably from about 180 to 1000, more preferably at least 200, yet more preferably at least 300 and most preferably around 480.

The MEL or MFI crystalline silicate catalyst may be mixed with a binder, preferably an inorganic binder, and shaped to a desired shape, e.g. extruded pellets. The binder is selected so as to be resistant to the temperature and other conditions employed in the catalyst manufacturing process and in the subsequent catalytic cracking process for the olefins. The binder is an inorganic material selected from clays, silica, metal oxides such as $ZrO_2$ and/or metals, or gels including mixtures of silica and metal oxides. The binder is preferably alumina-free, although aluminum in certain chemical compounds as in $AlPO_4$'s may be used as the latter are quite inert and not acidic in nature. If the binder which is used in conjunction with the crystalline silicate is itself catalytically active, this may alter the conversion and/or the selectivity of the catalyst. Inactive materials for the binder may suitably serve as diluents to control the amount of conversion so that products can be obtained economically and orderly without employing other means for controlling the reaction rate. It is desirable to provide a catalyst having a good crush strength. This is because in commercial use, it is desirable to prevent the catalyst from breaking down into powder-like materials. Such clay or oxide binders have been employed normally only for the purpose of improving the crush strength of the catalyst. A particularly preferred binder for the catalyst of the present invention comprises silica or $AlPO_4$.

The relative proportions of the finely divided crystalline silicate material and the inorganic oxide matrix of the binder can vary widely. Typically, the binder content ranges from 5 to 95% by weight, more typically from 20 to 50% by weight, based on the weight of the composite catalyst. Such a mixture of crystalline silicate and an inorganic oxide binder is referred to as a formulated crystalline silicate. In mixing the catalyst with a binder, the catalyst may be formulated into pellets, spheres, extruded into other shapes, or formed into a spray-dried powder.

In the catalytic cracking process of the OCP reactor, the process conditions are selected in order to provide high selectivity towards propylene or ethylene, as desired, a stable olefin conversion over time, and a stable olefinic product distribution in the effluent. Such objectives are favoured by the use of a low acid density in the catalyst (i.e. a high Si/Al atomic ratio) in conjunction with a low pressure, a high inlet temperature and a short contact time, all of which process parameters are interrelated and provide an overall cumulative effect.

The process conditions are selected to disfavour hydrogen transfer reactions leading to the formation of paraffins, aromatics and coke precursors. The process operating conditions thus employ a high space velocity, a low pressure and a high reaction temperature. The LHSV ranges from 0.5 to 30 $hr^{-1}$ preferably from 1 to 30 $hr^{-1}$. The olefin partial pressure ranges from 0.1 to 2 bars, preferably from 0.5 to 1.5 bars (absolute pressures referred to herein). A particularly preferred olefin partial pressure is atmospheric pressure (i.e. 1 bar). The heavy hydrocarbon fraction feedstock is preferably fed at a total inlet pressure sufficient to convey the feedstocks through the reactor. Said feedstock may be fed undiluted or diluted in an inert gas, e.g. nitrogen or steam. Preferably, the total absolute pressure in the second reactor ranges from 0.5 to 10 bars. The use of a low olefin partial pressure, for example atmospheric pressure, tends to lower the incidence of hydrogen transfer reactions in the cracking process, which in turn reduces the potential for coke formation which tends to reduce catalyst stability. The cracking of the olefins is preferably performed at an inlet temperature of the feedstock of from 400° to 650° C., more preferably from 450° to 600° C., yet more preferably from 540° C. to 590° C., typically around 560° to 585° C.

In order to maximize the amount of ethylene and propylene and to minimize the production of methane, aromatics and coke, it is desired to minimize the presence of diolefins in the feed. Diolefin conversion to monoolefin hydrocarbons may be accomplished with a conventional selective hydrogenation process such as disclosed in U.S. Pat. No. 4,695,560 hereby incorporated by reference.

The OCP reactor can be a fixed bed reactor, a moving bed reactor or a fluidized bed reactor. A typical fluid bed reactor is one of the FCC type used for fluidized-bed catalytic cracking in the oil refinery. A typical moving bed reactor is of the continuous catalytic reforming type. As described above, the process may be performed continuously using a pair of parallel "swing" reactors. The heavy hydrocarbon fraction cracking process is endothermic; therefore, the reactor should be adapted to supply heat as necessary to maintain a suitable reaction temperature. Online or periodic regeneration of the catalyst may be provided by any suitable means known in the art.

The various preferred catalysts of the OCP reactor have been found to exhibit high stability, in particular being capable of giving a stable propylene yield over several days, e.g. up to ten days. This enables the olefin cracking process to be performed continuously in two parallel "swing" reactors wherein when one reactor is operating, the other reactor is undergoing catalyst regeneration. The catalyst can be regenerated several times.

The OCP reactor effluent comprises methane, light olefins and hydrocarbons having 4 carbon atoms or more. Advantageously said OCP reactor effluent is sent to a fractionator and the light olefins are recovered. Advantageously the hydrocarbons having 4 carbon atoms or more are recycled at the inlet of the OCP reactor, optionally mixed with the heavy hydrocarbon recovered from the effluent of the XTO reactor. Advantageously, before recycling said hydrocarbons having 4 carbon atoms or more at the inlet of the OCP reactor, said hydrocarbons having 4 carbon atoms or more are sent to a second fractionator to purge the heavies. In a preferred embodiment the light olefins recovered from the effluent of the XTO reactor and the light olefins recovered from the fractionator following the OCP reactor are treated in a common recovery section.

Optionally, in order to adjust the propylene to ethylene ratio of the whole process (XTO+OCP), ethylene in whole or in part can be recycled over the OCP reactor and advantageously converted into more propylene. This ethylene can either come from the fractionation section of the XTO reactor or from the fractionation section of the OCP reactor or from both the fractionation section of the XTO reactor and the fractionation section of the OCP reactor or even from the optional common recovery section.

Optionally, in order to adjust the propylene to ethylene ratio of the whole process (XTO+OCP), ethylene in whole or in part can be recycled over the XTO reactor where it combines with the oxygen-containing, halogenide-containing or sulphur-containing organic feedstock to form more propylene. This ethylene can either come from the fractionation section of the XTO reactor or from the fractionation section of the OCP reactor or from both the fractionation section of the XTO reactor and the fraction section of the OCP reactor or even from the optional common recovery section.

These ways of operation allow to respond with the same equipment and catalyst to market propylene to ethylene demand.

FIG. 1 illustrates a specific embodiment of the invention. The effluent of the XTO reactor is passed to a fractionator 11. The overhead, a C1-C3 fraction including the light olefins is sent via line 2 to a common recovery section (not shown). The bottoms (the heavy hydrocarbon fraction) are sent via line 3 to the OCP reactor. The effluent of the OCP reactor is sent via line 10 to a fractionator 8. The overhead, a C1-C3 fraction including the light olefins, is sent via line 9 to a common recovery section (not shown). The bottoms, hydrocarbons having 4 carbon atoms or more, are sent to a fractionator 5. The overhead, hydrocarbons having 4 to substantially 5 carbon atoms are recycled via line 4 at the inlet of the OCP reactor. The bottoms, hydrocarbons having substantially 6 carbon atoms or more, are purged via line 6.

The method of making the olefin products from an oxygenate feedstock can include the additional step of making the oxygenate feedstock from hydrocarbons such as oil, coal, tar sand, shale, biomass and natural gas. Methods for making oxygenate feedstocks are known in the art. These methods include fermentation to alcohol or ether, making synthesis gas, then converting the synthesis gas to alcohol or ether. Synthesis gas can be produced by known processes such as steam reforming, autothermal reforming and partial oxidization in case of gas feedstocks or by reforming or gasification using oxygen and steam in case of solid (coal, organic waste) or liquid feedstocks. Methanol, methylsulfide and methylhalides can be produced by oxidation of methane with the help of dioxygen, sulphur or halides in the corresponding oxygen-containing, halogenide-containing or sulphur-containing organic compound.

One skilled in the art will also appreciate that the olefin products made by the oxygenate-to-olefin conversion reaction using the molecular sieve of the present invention can be polymerized optionally with one or more comonomers to form polyolefins, particularly polyethylenes and polypropylenes. The present invention relates also to said polyethylenes and polypropylenes.

EXAMPLES

Example 1

A sample of zeolite ZSM-5 with Si/Al=13 with a crystal size<1 μm in H-form synthesized without template has been obtained from TRICAT®. The sample is hereinafter identified as Comparative I.

Example 2

A sample of zeolite ZSM-5 described in example 1 was steamed at 550° C. for 48 h. Steamed solid was treated by 3,14M solution of $H_3PO4$ for 18 h under reflux condition (4.2 liter/1 kg of zeolite). Then the solid was separated by filtering from the solution. Obtained solid was dried at 110° C. for 16 h and calcined at 400° C. for 10 h.

(Atomic ratio Si/Al-25, P-content 5.6 wt %). The sample is hereinafter identified as Sample A.

Example 3

This example contains a procedure for preparation of dealuminated ZSM-5 by steaming and leaching with phosphorus acid. However almost all P was removed by washing. Thus the zeolite was dealuminated by the same way but contained a very low P amount.

A sample was prepared using the same procedure as in example 2, except the sample was washed 6×2000 ml of distilled water per kg of zeolite. The sample was dried right away after the filtering at 110° C. for 16 h and calcined at 400° C. for 10 h.

(Atomic ratio Si/Al-26, P-content 0.2 wt %). The sample is hereinafter identified as Comparative II.

Example 4

This example contains a procedure for P-ZSM-5 preparation with a P-content close to in sample A. However in this case the order of steaming and treatment with phosphorus acid was inversed. In the same time, this recipe produces non-leached sample modified with phosphorous, meaning a total Al content in the zeolite after this treatment remained unchanged.

100 g of zeolite ZSM-5 described in example 1 was impregnated with 23 g of $H_3PO_4$ (85 wt % in water) at room temperature and dried at 110° C. for 16 h. Then the sample was calcined at 400° C. for 10 h. Finally, obtained solid was steamed at 550° C. for 48 h. (Atomic ratio Si/Al is 13 and P content 4 w %).

The sample is hereinafter identified as Comparative III.

Example 5

This example presents non-dealuminated ZSM-5 with the same atomic Si/Al ratio and P-content as in Sample A, but the P was introduced by impregnation.

A sample of zeolite ZSM-5 with Si/Al=25 with a crystal size<1 μm in H-form has been obtained from Zeolyst International. The sample was calcined at 550° C. for 6 h. Then the zeolite was impregnated by the incipient wetness method with an aqueous solution of $(NH_4)_2HPO_4$ with a target to introduce 5% of P in the sample. 60 g of the calcined zeolite was impregnated with a solution containing 47 g water and 13,461 g $(NH_4)_2HPO_4$. Finally the P-zeolite was dried overnight at 110° C. and calcined at 600° C. for 10 h. (Atomic ratio Si/Al is 25 and P content 5 w %).

The sample is hereinafter identified as Comparative VI.

Example 6

In this example P was introduced in zeolite during the leaching (dealumination).

A sample of zeolite ZSM-5 with Si/Al=13,8 with a crystal size<1 μm H-form has been obtained from Zeolyst. The sample was steamed at 680° C. for 2 h. The steamed solid was treated by 3.14 M solution of $H_{PO}4$ for 18h under reflux condition (4.2 liter/1 kg of zeolite). Then the solid was separated by filtering from the solution and dried at 400° C. for 3 h in air. Then the dried sample was subjected in a contact with a hot water solution under reflux condition for 2 h. Then the solid was separated by filtering from the solution and dried right away at 110° C. for 16 h and steamed at 600° C. for 2 h (Atomic ratio Si/Al-21, P-content 1.8 wt %).

The sample is hereinafter identified as Sample B.

Example 7

This example presents a recipe for P-ZSM-5 dealuminated by steaming and treatment with phosphorous acid and some additional P was introduced after dealumination by impregnation.

A sample was prepared using the same procedure as in example 6, except after the leaching and filtering steps the solid was washed with 2000 ml of distilled water per kg of zeolite (P content>0.3 wt %).

Then 53.67 g of the sample was mixed with 225.4 ml of water contained 4.064 g of $(NH_4)H_2PO_4$. Then the solution containing the zeolite and $(NH_4)H_2PO_4$ was evaporated under stirring. Obtained solid was dried at 110° C. for 16 h and steamed at 600° C. for 2 h. (Atomic ratio Si/Al-21, P content 2,10 wt %).

The sample is hereinafter identified as Sample C.

Example 8-9

XTO Conditions (XTO in the Table)

Catalyst tests were performed on 2 g catalyst samples with a pure methanol feed in a fixed-bed, down flow stainless-steel reactor. Catalyst powders was pressed into wafers and crushed to 35-45 mesh particles. Prior to catalytic run all catalysts were heated in flowing $N_2$ (5 Nl/h) up to the reaction temperature. Analysis of the products has been performed on-line by a gas chromatograph equipped with a capillary column. The catalyst performances were compared at substantially full methanol conversion, under equal conditions and maximum propylene yield. The results are displayed on carbon and water free basis.

OCP Conditions (XTO+OCP in the Table)

The feedstock which contains substantially non cyclic olefins C4+ (the heavy hydrocarbon fraction) was subjected to catalytic cracking (the second reactor) in the presence of an aluminosilicate catalyst in a fixed bed reactor at 575° C., LHSV=10 $h^{-1}$, P=1.5 bara. This catalyst comprises a commercially available silicalite which had been subjected to a dealumination treatment by combination of steaming with acid treatment so as provide Si/Al ratio ~250. A detailed procedure of catalyst preparation is described in above cited EP1194502 B1.

The OCP performance has been simulated using a mathematic model employing conversion factors deduced from numerous testing of different feedstocks. Based on the stream composition going to the OCP reactor and on the required purges an optimum stream of C4 and heaviers are recycled around the OCP reactor. The lines under "OCP feed non cyclic olefins C4+" display the heavy hydrocarbon flow rate sent to the OCP (the second reactor). The lines under "XTO+ OCP" display the ethylene and propylene produced by the combination of the primary reactor (MTO) and the second reactor (OCP).

The values in table are the weight percent on carbon basis.

| Example 8 | | | |
|---|---|---|---|
| | Comparative I ZSM-5 | Comparative II P-ZSM-5 | Sample A P-ZSM-5 |
| Si/Al | 13 | 26 | 25 |
| P, % | 0 | <0.2 | 5.6 |
| XTO | | | |
| T, ° C. | 450 | 450 | 450 |
| WHSV, $h^{-1}$ | 1.6 | 1.6 | 1.6 |
| P, barg | 0.5 | 0.5 | 0.5 |
| C1 (methane) | 3.4 | 1.2 | 1.3 |
| Paraffins | 51.6 | 37.0 | 11.2 |
| Olefins | 29.2 | 54.0 | 69.2 |
| Dienes | 0.0 | 0.3 | 1.5 |
| Aromatics | 19.2 | 8.8 | 6.6 |
| C3−/C2− | 1.6 | 2.3 | 4.8 |
| C2− + C3− | 6.7 | 23 | 28 |
| ethylene | 2.6 | 7 | 5 |
| propylene | 4.1 | 16 | 23 |
| OCP feed (non cyclic olefins C4+) | | | |
| Σ olefins | 18 | 28 | 40 |
| XTO + OCP | | | |
| C3−/C2− | 2.8 | 2.9 | 4.3 |
| C2− + C3− | 20 | 43 | 58 |
| ethylene | 5 | 11 | 11 |
| propylene | 15 | 32 | 47 |

| Example 9 | | | |
|---|---|---|---|
| | Comparative III P-ZSM-5 | Comparative VI P-ZSM-5 | Sample A P-ZSM-5 |
| Si/Al | 13 | 25 | 25 |
| P, % | 4 | 5 | 5.6 |
| XTO | | | |
| T, ° C. | 550 | 550 | 550 |
| WHSV, $h^{-1}$ | 1.6 | 1.6 | 1.6 |
| P, barg | 0.5 | 0.5 | 0.5 |
| C1 (methane) | 6.4 | 2.3 | 1.6 |
| Paraffins | 11.7 | 4.7 | 5.5 |
| Olefins | 73.0 | 82.1 | 86.1 |
| Dienes | 1.1 | 1.6 | 1.9 |
| Aromatics | 14.2 | 6.0 | 5.2 |
| C3−/C2− | 2.0 | 4.8 | 5.0 |
| C2− + C3− | 47 | 45 | 46 |
| ethylene | 15 | 8 | 8 |
| propylene | 32 | 37 | 38 |
| OCP feed (Non cyclic olefins C4+) | | | |
| Σ olefins | 25 | 36 | 39 |
| XTO + OCP | | | |
| C3−/C2− | 2.5 | 4.5 | 4.4 |
| C2− + C3− | 66 | 71 | 75 |

-continued

Example 9

| | Comparative III<br>P-ZSM-5 | Comparative VI<br>P-ZSM-5 | Sample A<br>P-ZSM-5 |
|---|---|---|---|
| ethylene | 19 | 13 | 14 |
| propylene | 47 | 58 | 61 |

Figure 2:
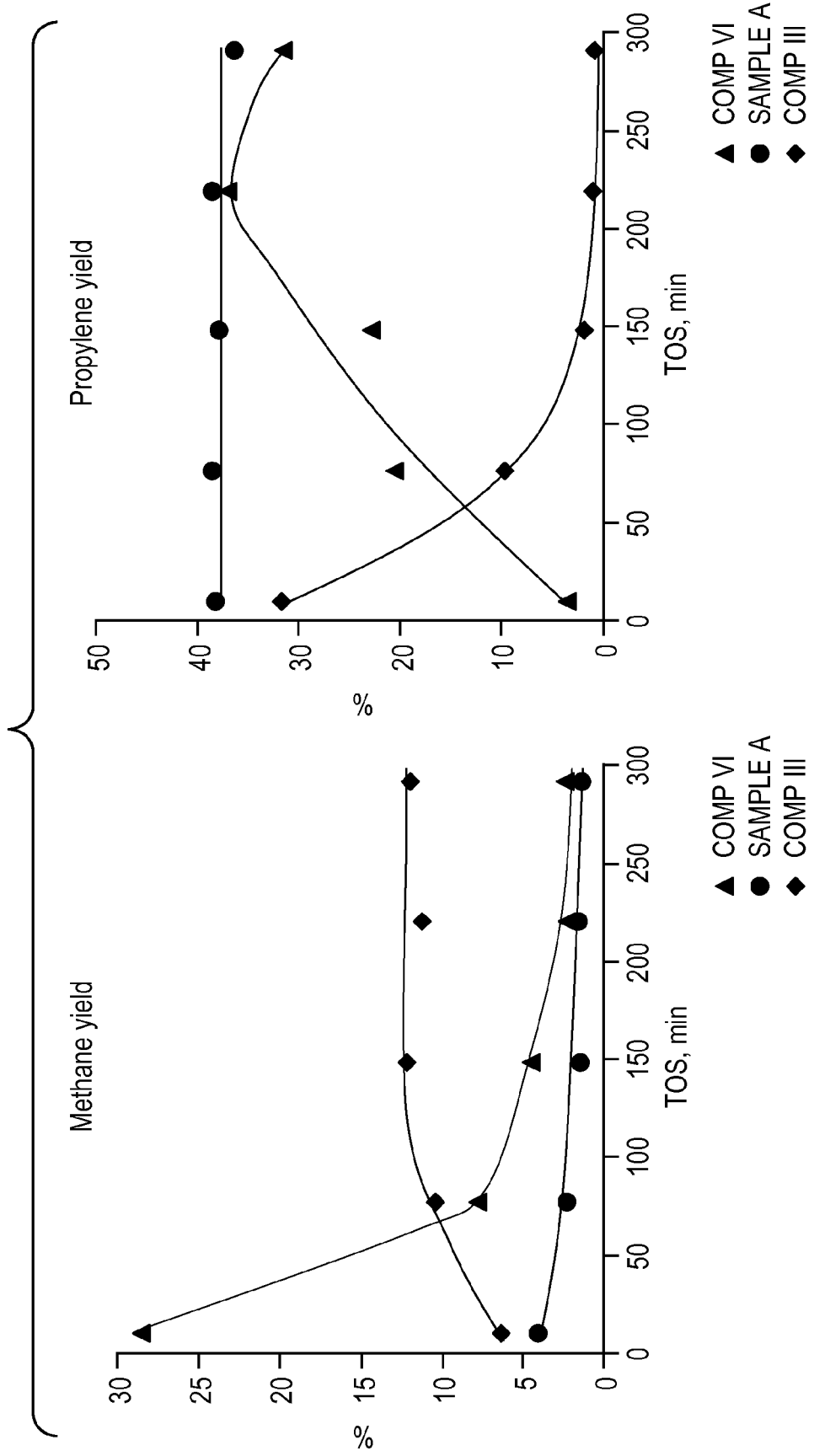

Methane yield and propylene yield vs time on stream (TOS) are on FIG. 2. It is clear from the FIG. 2 that the comparative examples 3 and 4 do not result in stable propylene production.

Example 10

XTO Conditions (XTO in the Table)

Catalyst tests were performed on 2 g catalyst samples with a pure methanol feed in a fixed-bed, down flow stainless-steel reactor. Catalyst powders was pressed into wafers and crushed to 35-45 mesh particles. Prior to catalytic run all catalysts were heated in flowing $N_2$ (5 Nl/h) up to the reaction temperature. Analysis of the products has been performed on-line by a gas chromatograph equipped with a capillary column. The catalyst performances were compared at full methanol conversion, under equal conditions and maximum propylene yield. The results are displayed on carbon and water free basis.

Example 10

| | Sample C<br>P-ZSM-5 | Sample B<br>P-ZSM-5 |
|---|---|---|
| Si/Al | 21 | 21 |
| P, % | 2.1 | 1.8 |
| T, ° C. | 550 | 550 |
| WHSV, h$^{-1}$ | 1.6 | 1.6 |
| P, barg | 0.5 | 0.5 |
| XTO | | |
| C1 (methane) | 3.4 | 2.0 |
| Paraffins | 5.9 | 5.6 |
| Olefins | 83.7 | 80.6 |
| Dienes | 1.3 | 0.9 |
| Aromatics | 8.3 | 11.8 |
| C3−/C2− | 4.5 | 2.7 |
| C2− + C3− | 48 | 52 |
| ethylene | 9 | 14 |
| propylene | 39 | 38 |
| OCP feed (Non cyclic olefins C4+) | | |
| Σ olefins | 35 | 28 |

Example 11

(OCP)

Catalyst tests were performed on 10 ml (~6 g) of catalyst grains (35-45 meshes) (Sample A) loaded in the tubular reactor. The feedstock which contains substantially non cyclic olefins C4 (~60%) was subjected to catalytic cracking in the presence of catalyst in a fixed bed reactor at 550° C., LHSV=2 h$^{-1}$, P=1.5 bara. The results are in table 1 hereunder. The values in table 1 are the weight percent on carbon basis.

The data given below illustrate a cracking activity of the Sample A in C4 olefins conversion to propylene and ethylene at the same temperature and pressure as in XTO reactor.

| | SAMPLE A | |
|---|---|---|
| | feed | effluent |
| Paraffins | 41.1 | 41.5 |
| Olefins | 58.8 | 55.5 |
| Dienes | 0.0 | 0.7 |
| Aromatics | 0.0 | 2.3 |
| C1 (methane) | 0.0 | 0.4 |
| Ethylene | 0.0 | 5.0 |
| Propane | 0.6 | 1.4 |
| Propylene | 0.3 | 20.8 |
| Butenes | 57.4 | 19.2 |

The invention claimed is:

1. A method of making a phosphorous modified zeolite, comprising:
   selecting a zeolite having a Si:Al atomic ratio of 30 or less, wherein the zeolite is selected from the group consisting of MFI, MEL, FER, MOR, and clinoptilolite, and wherein the selected zeolite is in the $H^+$ or $NH_4^+$ form;
   steaming the zeolite at a temperature ranging from 400° C. to 870° C. for 0.01 h to 200 h;
   leaching the zeolite with an aqueous acid solution containing a source of P at conditions effective to remove a substantial amount of Al from the zeolite and to introduce more than 0.3 wt % of P, wherein the aqueous acid solution containing the source of P comprises a salt of a phosphate ($[PO_4]^{3-}$), an acid or a corresponding salt of a phosphite ($[HPO_3]^{2-}$), an acid or a corresponding salt of a hypophosphite ($[H_2PO_2]^{1-}$), an acid or a corresponding salt of a diphosphate, or an acid or a corresponding salt of a polyphosphate;
   separating the zeolite from the aqueous acid solution; and
   calcining the zeolite.

2. The method of claim 1, wherein the zeolite is an MFI zeolite.

3. The method of claim 1, wherein the phosphorus modified zeolite has been made without direct addition of organic template.

4. The method of claim 1, wherein the zeolite has an initial Si:Al atomic ratio ranging from 4 to 30.

5. The method of claim 1, wherein the steaming step is performed at a temperature ranging from 480 to 760° C.

6. The method of claim 1, wherein the steaming step is carried out for a period of from 0.05 to 200 hours.

7. The method of claim 6, wherein the steaming step is carried out for a period of from 0.05 to 50 hours.

8. The method of claim 1, wherein the step of leaching with the aqueous acid solution containing the source of P is conducted under boiling conditions of the solution.

9. The method of claim 1, wherein the separated zeolite is subjected to a washing step or a combination of a washing step and a drying step.

10. The method of claim 9, wherein the separated zeolite is dried at a temperature between 40 and 600° C.

11. The method of claim 1, wherein the leaching period is 0.5 to 24 hours.

12. The method of claim 1, wherein the aqueous acid solution containing the source of P in the leaching step has a pH of 3 or lower.

13. The method of claim 12, wherein the aqueous leaching acid solution comprises phosphorus acids, a mixture of phosphorus acids and organic or inorganic acids, or a mixture of salts of phosphorus acids and organic or inorganic acids.

14. The method of claim 1, wherein the final P content of the phosphorus modified zeolite is up to 7 wt %.

15. The method of claim 1, wherein at least 10% of the Al present in the zeolite has been extracted and removed by leaching.

16. The method of claim 2, wherein the MFI zeolite is a ZSM-5.

17. The method of claim 1, wherein the final P content of the phosphorus modified zeolite is at least about 1.8 wt %.

18. The method of claim 17, wherein the final P content of the phosphorus modified zeolite is up to 7 wt %.

19. The method of claim 1, wherein the aqueous acid solution containing the source of P comprises an acid or a corresponding salt of a phosphite ($[HPO_3]^{2-}$), an acid or a corresponding salt of a hypophosphite ($[H_2PO_2]^{1-}$), an acid or a corresponding salt of a diphosphate, or an acid or a corresponding salt of a polyphosphate.

20. A method of making a phosphorous modified zeolite, comprising:
- selecting a zeolite having a Si:Al atomic ratio of 30 or less, wherein the zeolite is selected from the group consisting of FER, MOR, and clinoptilolite, and wherein the selected zeolite is in the $H^+$ or $NH_4^+$ form;
- steaming the zeolite at a temperature ranging from 400° C. to 870° C. for 0.01 h to 200 h;
- leaching the zeolite with an aqueous acid solution containing a source of P at conditions effective to remove a substantial amount of Al from the zeolite and to introduce at least 0.3 wt % of P;
- separating the zeolite from the aqueous acid solution; and
- calcining the zeolite.

21. The method of claim 1, wherein the aqueous acid solution containing the source of P comprises phosphorous acid ($H_3PO_3$).

* * * * *